United States Patent [19]

Drennan et al.

[11] 4,372,300

[45] Feb. 8, 1983

[54] CAST WEDGE

[75] Inventors: Denis B. Drennan, Evanston; Donald J. Maylahn, Skokie; Thomas R. Schleicher, Wilmette, all of Ill.

[73] Assignee: DM Systems, Inc., Evanston, Ill.

[21] Appl. No.: 263,264

[22] Filed: May 13, 1981

[51] Int. Cl.³ .............................................. A61F 5/04
[52] U.S. Cl. ..................................... 128/83; 128/91 R
[58] Field of Search ............... 128/83, 87 R, 90, 91 R, 128/91 A, 136

[56] References Cited

U.S. PATENT DOCUMENTS 725,354 4/1903 Nicholls ............................ 128/136
3,307,539 3/1967 Petersen ............................ 128/136

Primary Examiner—John D. Yasko

Attorney, Agent, or Firm—Mason, Kolehmainen, Rathburn & Wyss

[57] ABSTRACT

A cast wedge for use in adjusting a tubular cast for maintaining predetermined spacing between opposite facing edges of a transverse cut made in the cast wall adjacent the area of the limb fracture. The wedge includes a body formed of molded, resinous plastic material that is radio-lucent having a wedge portion with opposite edges spaced a predetermined distance apart for direct engagement with the facing edges of the cut in the wall of the cast. Flanges are formed to extend outwardly and normal to the opposite edges of the wedge portion and the flanges have an inside surface engageable with the outer surface of the cast for limiting the inward travel of the wedge portion into the interior of the cast.

12 Claims, 5 Drawing Figures

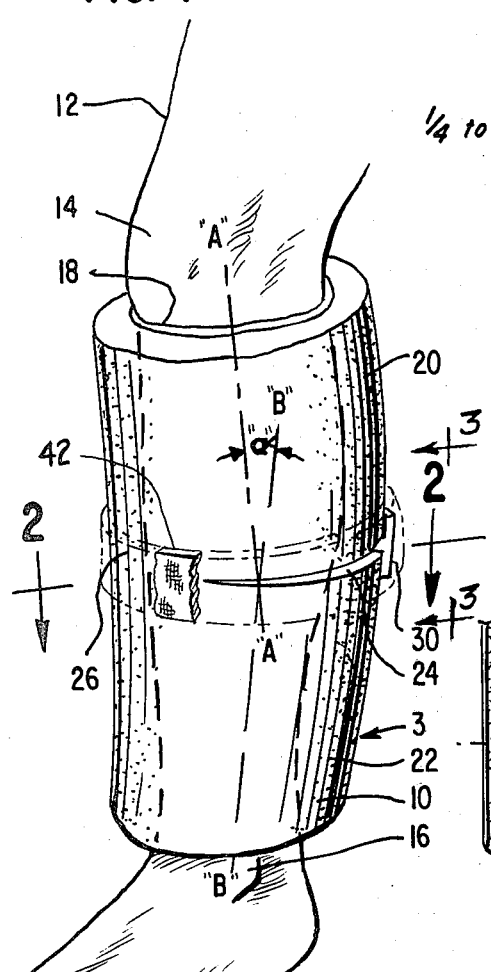
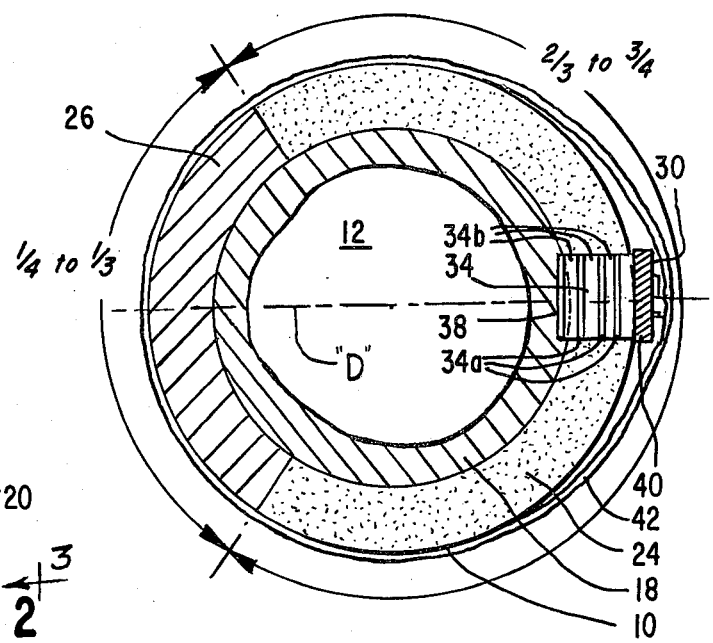
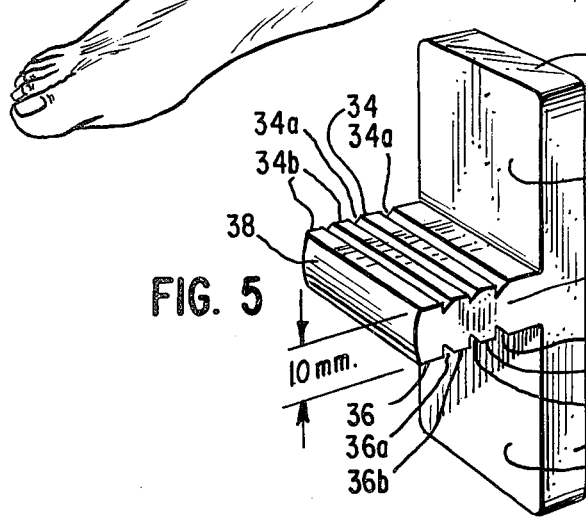
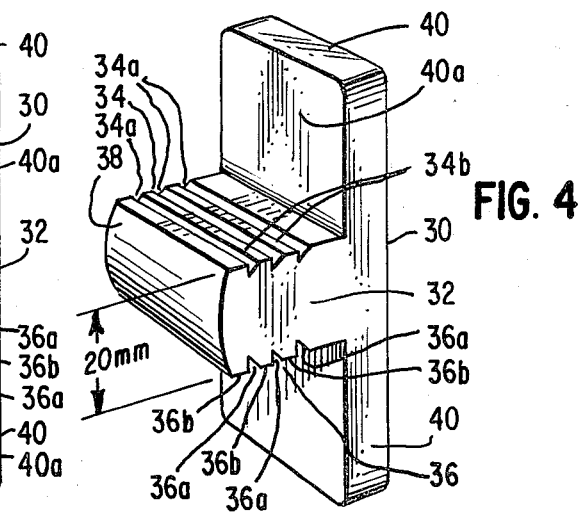

CAST WEDGE

BACKGROUND OF THE INVENTION

1. Field of the Invention

The present invention relates to a new and improved wedge for use with tubular casts commonly provided for the treatment of fractured limbs. More particularly, the cast wedge of the present invention is especially suited and adapted for use in connection with limb casts formed of wrapped cloth impregnated with Plaster of Paris.

2. Description of the Prior Art

In treating limb fractures, physicians often employ tubular casts for immobilizing the fracture and these casts are constructed around the broken bone by first wrapping the limb with cotton gauze or other suitable dressing material on both sides of the fracture area followed by the application of a cloth wrapping impregnated with wet Plaster of Paris which hardens in a short time after the wrapping has been completed.

The hardened Plaster of Paris provides a firm, rigid tubular cast which supports the broken limb on both sides of the fracture area and provides the desired immobilization of the fracture so that the bone may begin to heal and knit together. Often times as the healing process continues, it is desirable to adjust the longitudinal alignment of the bone portions on opposite sides of the fracture area and this is often done without removing the existing cast from the broken limb. An alternative procedure would entail completely removing the existing cast and then constructing a new cast on the limb with the desired shape to achieve the intended bone alignment.

The procedure which does not require removal of the existing cast is usually faster, cheaper and more accurate in producing the precise and necessary adjustments in bone alignment within the cast to promote the best knitting of the fractured bone.

In this process, a transverse cut is made in the wall of the cast about ⅔ to ¾ of the way around the complete circumference, but leaving a small portion of the cast (the remaining ⅓ or ¼) intact without cutting. This uncut portion serves as a hinge between the portions of the cast on opposite sides of the transverse cut.

In the prior art, various types of spacers or wedges were then inserted between the facing edges of the cut in the cast directly opposite the uncut hinge portion. These wedges provided the desired amount of spacing to form a precise degree of angular adjustment between the portions of the cast on opposite sides of the cut. These wedges are often made of wood, dowels, sheet padding, Plaster of Paris and anything handy in the cast room, usually on an ad hoc basis. After insertion of a wedge it is held in place only by additional wrapping of cloth impregnated by Plaster of Paris. Often times it is necessary to repeat the procedure and provide sucessive transverse cuts in the cast wall and different wedges to progressively change the angular adjustment of the cast portions as healing of the fracture proceeds.

One of the problems associated with this type of procedure is the lack of readily available, objects for use as wedges or spacers. Another problem is the tendency of some of the objects often used such as pieces of wood, splints or gauze padding to move relative to the cast or change shape after installation. In some cases, these objects change or permit change in the spacing interval between the opposite facing edges of the cut in the cast wall. Moreover, wedging objects of a particular size are not readily available and fabrication of wedges or spacers requires additional physician time.

U.S. Pat. No. 2,295,253 is directed to a fracture aligner in which windows are cut in the wall of a tubular cast so that selectively adjustable pressure pads can be applied to effect bone displacement. This type of cast may result in a relatively high concentration of pressure on a relatively small area on the surface of the limb adjacent the fracture.

OBJECTS OF THE PRESENT INVENTION

It is an object of the present invention to provide a new and improved wedge for use with tubular casts, and more particularly, a new and improved cast wedge system especially adapted for use with Plaster of Paris casts that are commonly used in treating limb fractures.

Another object of the present invention is to provide a new and improved cast wedge of the character described having a wedge portion of predetermined size adapted to be inserted between the facing opposite the surfaces of a transverse cut made in a cast and an outer flange portion engagable with outside surfaces of the cast to limit the inward travel of the wedge into the cut.

Yet another object of the present invention is the provision of a new and impoved cast wedge of the character described having a presized wedge portion with indicia thereon corresponding to the spacing or dimension between opposite edges that engage the cut surfaces of the cast wall.

Still another object of the present invention is to provide a new and improved cast wedge of the character described which is formed with teeth or serrations on the opposite wedge surfaces for biting or holding engagement with the adjacent edges of the cast material.

Yet another object of the present invention is to provide a new and improved cast wedge of the character described which is formed with a crowned or convex inner end surface on the wedge portion to facilitate insertion of the wedge into place in a transverse cut made in a tubular cast.

Still another object of the present invention is to provide a new and improved cast wedge formed of molded plastic material which is light in weight, extremely strong and which is radio-lucent so that it does not interfere with normal X-ray procedures.

Still another object of the present invention is to provide a new and improved cast wedge of the character described which provides greater accuracy in making precise angular adjustments in tubular casts and which permits angular cast adjustments to be accomplished in a much shorter time and yet in a more controllable manner than heretofore possible.

Yet another object of the present invention is to provide a new and improved cast wedge system including a plurality of cast wedges of the character described, each having a different wedge size so that a wide range of angular cast adjustments can be achieved.

BRIEF SUMMARY OF THE INVENTION

The foregoing and other objects and advantages of the present invention are accomplished in an illustrated embodiment thereof comprising a wedge for use with tubular casts for maintaining a predetermined spacing distance between opposite, facing edges formed in a transverse cut made in the cast in the region of the fractured limb in order to facilitate angular adjustment of the cast portions on opposite sides of the cut. The wedge includes a body formed of strong, light, radiolucent, molded plastic material having a wedge portion formed with opposite edges spaced a predetermined distance apart for direct engagement with the facing edges of the transverse cut in the cast wall. The wedge includes outer flanges extending normal to the opposite edges of the wedge portion and these flanges have inside faces of substantial area engagable with the outer surface of the cast adjacent the cut edges for limiting the inward travel of the wedge into the cast wall. The cast engaging edges of the wedge portion are formed with a plurality of serrations of ribs and groove for biting into the edges of the cast wall. An inner end surface of the wedge portion is formed with a convex shape to facilitate insertion of the wedge into the transverse cut in the cast wall. A plurality of cast wedges are provided in a set, some with diferent dimensions or spacing between the opposite edge surfaces of the wedge portion and appropriate identifying numbers are provided on the outer surface of the wedges to indicate the particular size of the wedge.

BRIEF DESCRIPTION OF THE DRAWINGS

For a better understanding of the invention, reference should be had to the following detailed description taken in conjunction with the drawings, in which:

FIG. 1 illustrates a typical, tubular cast formed of Plaster of Paris and shown in position on the leg of a patient with a cast wedge constructed in accordance with the features of the present invention inserted in a transverse cut made in the cast wall;

FIG. 2 is a transverse, cross-sectional view taken substantially along lines 2—2 of FIG. 1;

FIG. 3 is a fragmentary, rear elevational view taken as if looking in the direction of the arrows 3—3 of FIG. 1; and FIGS. 4 and 5 are enlarged perspective views of a plurality of cast wedges of different size constructed in accordance with the features of the present invention.

DESCRIPTION OF A PREFERRED EMBODIMENT

Referring now to the drawings, therein is illustrated a typical, Plaster of Paris, limb cast 10 of hollow, tubular, transverse cross-section and shown in position on the lower leg 12 of a patient between the knee 14 and the ankle 16. Typically, the elongated tubular limb cast is constructed by first applying a wrapping of soft, gauze or cotton dressing material 18 around the limb in the area where the cast will be applied to immobilize the fracture. The dressing material provides a relatively soft cushion between the skin and the cast, and presents high pressure points or areas from developing between the hard inner surface of the cast and the relatively soft surface of the skin.

After the dressing material in suitable thickness is applied, the cast 10 is formed by wrapping cloth or woven material around the dressing, which cloth is impregnated with Plaster of Paris not yet hardened. When the Plaster of Paris hardens, a rigid tubular shell is formed to encase the limb between the knee and ankle as shown. The cast extends in opposite directions from the fracture area of the bone, both above and below the general area of the leg fracture which is generally designated at the level of the cross-section lines 2—2 in FIG. 1.

As the fractured bone begins to knit and heal, it may be necessary to angularly adjust upper and lower segments 20 and 22 of the cast, so that longitudinal, central axes "A—A" and "B—B" thereof will angularly intersect one another and diverge as indicated by the angle "alpha".

In accordance with the present invention, this angular adjustment may be obtained without requiring removal or destruction of the cast 10. This is done by making a transverse cut 24 in the cast wall around approximately ⅔ to ¾ of the total circumference at the level of the bone fracture region. The remaining ⅓ of ¼ of the circumference. of the cast wall (as designated by the reference numeral 26) remains intact and serves as a hinge portion continuously interconnecting the partially severed, upper and lower segments 20 and 22. The respective longitudinal axes "A—A" and "B—B" of these segments may be manually adjusted to a desired angle "alpha" of intersection in the region of the bone fracture and in order to maintain a precise degree of angular adjustment, a new and improved cast wedge 30, constructed in accordance with the features of the present invention, is inserted into the transverse cut 24 in the wall of the cast 10 at a position diametrically opposite the hinge portion 26 as best shown in FIG. 2.

Preferably, the cast wedges 30 are formed of molded, resinous plastic material such as polystyrene, polyvinyl chloride or polyethylene and a material is chosen that is radio-lucent so that X-rays taken with a wedge or wedges in place in the cast will not effect or obscure the fracture. Each cast wedge includes an inwardly extending wedge portion 32 having a pair of spaced apart, opposite wedge surfaces 34 and 36. The surfaces are spaced apart by a preselected or predetermined distance such as 10, 15, 20, 25, 30 millimeters, etc. . . to provide a desired range of spacing interval between 10 and 30 mm, for example. Depending on the diameter of the cast, a 10 mm. wedge may provide a 5° angle of divergence between the axes "A—A" and "B—B", and a 15 mm. wedge would provide a proportionately larger angle.

The wedge portion 32 is formed with a crowned or rounded, convex inner end surface 38 for facilitating the insertion of the wedge portion into the transverse cut 24 provided in the cast wall. Each wedge surface 34 and 36 is formed with a plurality of saw-tooth, like serrations or grooves (34a and 36a respectively) and these grooves define sharpened teeth or ridges (34b and 36b respectively) which bite into the exposed, opposite, facing edge surfaces of the transverse cut 24 on the upper and lower sections 20 and 22 of the cast wall. The biting engagement of the teeth 34b and 36b securely hold the wedge portion 32 in place in the cast wall after insertion.

In order to limit the amount of inward penetration of the wedge portion 32 into the interior of the cast 10, each wedge 30 includes a pair of upper and lower flanges 40, each with an inside face 40a having a relatively large surface area adapted to bear against the outside wall surface of the cast 10 adjacent the transverse cut 24. This provides a relatively low pressure engagement between the wedge and the cast material and positively limits the inward penetration of the wedge portion 32 toward the limb without crushing the edge of the cast around the cut. Once a desired size of wedge is chosen and inserted into place, as shown in FIGS. 1 and 2, the angle of adjustment between the axes "A—A" and "B—B" may be measured and if correct, the inserted wedge 30 is then secured in place within the transverse cut 24 by wrapping additional layers 42 of cloth or gauze around the outside of the cast and the outer surface of the wedge. The wrapping material is impregnated with wet Plaster of Paris which subsequently hardens to form a rigid cover over the flanges 42 of the wedge and closes the opening formed by the cut 24 in the cast wall.

In accordance with the invention, an outside surface 30a of the wedges is relatively flat and is provided with indicia 44 thereon for indicating the size of the wedge, particularly the distance or spacing between the wedge surfaces 34 and 36 on the wedge portion 32. A set of wedges 30 for leg casts may include wedges having incremental spacing values of 10 through 30 millimeters at 5 millimeter intervals. When spacing intervals other than these are needed to provide a particular angle of divergence between the axes "A—A" and "B—B", the radial position of the wedge relative to the hinge portion 26 may be changed or selected to provide a greater spacing distance.

Referring to FIG. 3, a 10 millimeter size wedge 30 may be inserted into the transverse 24 cut at a radial position spaced away from a diametrical plane "D" passing through the cast on the axes "A—A" and "B—B", and the center of the hinge portion 26. Movement of a wedge away from this diametral plane, will open the spacing of the cut to a distance "Y" as measured on the diametral plane, and the distance "Y" is necessarily greater than the 10 millimeter spacing distance "X" provided by the wedge when positioned directly opposite the hinge portion 26 on the diametral plane "D".

A pair of wedges 30 may be used if desired, and when the wedges are placed in position on opposite sides of the diametral plane as shown in FIG. 3 a compound angle of adjustment between the longitudinal axes of the cast sections 20 and 22 may be achieved. Generally, a single wedge is sufficient and after one size of wedge has been used, if it is desired to subsequently adjust the angular displacement between the upper and lower sections 20 and 22 of the cast 10, another cut may be made and an additional wedge inserted. An inserted wedge may be moved to a different radial position when desired to achieve a greater or lesser space to increase or decrease the amount of angular deflection between the cast segments 20 and 22.

Although the present invention has been described with reference to a single illustrated embodiment thereof, it should be understood that numerous other modifications and embodiments can be devised by those skilled in the art that will fall within the spirit and scope of the principles of this invention.

What is claimed as new and desired to be secured by Letters Patent of the United States is:

1. A wedge for use with a tubular cast for maintaining a space between opposite facing edges formed by a transverse cut in said cast, comprising:
   a body formed of molded plastic material having opposite edges spaced a predetermined distance apart for engagement, with said facing cut edges of said cast; and
   flange means extending normal to said opposite edges and outwardly thereof having a face engageable with an outer surface of said cast adjacent said cut edges for limiting the inward movement of said body into said cast,
   said body and said flange means having pairs of substantially coplanar opposite side surfaces normal to said face of said flange means and normal to said opposite edges of said body whereby said body is visible from a side during insertion into a cut in a cast.

2. The cast wedge of claim 3 wherein said body is formed with a convex inner end surface between said opposite edges facilitating insertion of said body into said cut of said cast.

3. A wedge for use with a tubular cast for maintaining a space between opposite facing edges formed by a transverse cut in said cast, comprising:
   a body formed of molded plastic material having opposite edges spaced a predetermined distance apart for engagement with said facing cut edges of said cast, said opposite edges of said body being formed with a plurality of alternate ribs and grooves for facilitating the holding engagement between said edges and said facing cut edges of said cast, and
   flange means extending normal to said opposite edges and outwardly thereof having a face engageable with an outer surface of said cast adjacent said cut edges for limiting the inward movement of said body into said cast.

4. The cast wedge of claim 3 wherein said alternate ribs and grooves provide teeth for biting engagement into said cut edges of said cast for biasing said flange means against said outer surface of said cast.

5. The cast wedge of claim 4 wherein said teeth have a triangular shaped, transverse cross-section with intersecting surfaces generally parallel of said faces of said flange means and sloping away from faces toward a central portion of said body.

6. A plurality of cast wedges of claim 3 in a set with different wedges in said set, each wedge having a different spacing distance between said opposite edges of said body.

7. The set of cast wedges of claim 6 including identifying means on each wedge indicative of the particular spacing distance between said opposite edges of said body of said wedge.

8. The set of cast wedges of claim 6 or 7 wherein said different spacing distances comprise equal spacing increments between a minimum and maximum value for the set.

9. The cast wedge of claim 3 or 2 wherein said flange means includes a pair of flanges extending in opposite directions normal to said respective opposite edges of said body, said flanges and said body having a unitary outer surface.

10. The cast wedge of claim 9 including identifying means on said outer surface indicative of the spacing distance between said opposite edges of said body.

11. The cast wedge of claim 3 wherein said material is radio lucent.

12. The cast wedge of claim 3 or 11 wherein said material is polystyrene, polyvinylchloride or polyethylene.

* * * * *